United States Patent [19]

Anthony

[11] Patent Number: 5,087,120
[45] Date of Patent: Feb. 11, 1992

[54] SYSTEM FOR CAPTURING, PRESSING AND ANALYZING ENTRAINED SOLIDS SUCH AS COTTON

[75] Inventor: William S. Anthony, Greenville, Miss.

[73] Assignee: The United States of America as represented by the Secretary of Agriculture, Washington, D.C.

[21] Appl. No.: 641,837

[22] Filed: Jan. 16, 1991

[51] Int. Cl.$^5$ .................. G01N 1/20; G01N 21/47
[52] U.S. Cl. .................... 356/36; 250/576; 356/244; 356/445
[58] Field of Search ............... 356/36, 38, 244, 445; 250/574, 576

[56] References Cited
U.S. PATENT DOCUMENTS

| | | | |
|---|---|---|---|
| 3,224,324 | 12/1965 | Coppock et al. | 356/445 |
| 3,869,213 | 3/1975 | Greene | 356/244 |
| 3,943,771 | 3/1976 | Handa et al. | 356/36 X |
| 4,154,533 | 5/1979 | Levine | 356/36 X |

Primary Examiner—Vincent P. McGraw
Attorney, Agent, or Firm—M. Howard Silverstein; John D. Fado

[57] ABSTRACT

A system for analyzing bulk cotton or other flowable solids comprising moving the cotton through a conduit; halting part of the cotton within the conduit while permitting the remaining part to continue movement through the conduit; moving the halted mass in an arcuate pathway toward an interior surface of the conduit; pressing the halted mass against the interior surface; wherein the pressing means is sufficient to press the mass against the interior surface to form a face of uniform cotton density on that part of the mass which is pressed against the interior surface; analyzing such face for a property selected from the group consisting of color, trash content, moisture content, and combinations thereof; and thereafter releasing the pressure on the halted mass to allow it to resume movement through the conduit.

30 Claims, 2 Drawing Sheets

SYSTEM FOR CAPTURING, PRESSING AND ANALYZING ENTRAINED SOLIDS SUCH AS COTTON

FIELD

The present invention relates to analyzing flowable solids such as cotton passing through a gin.

PRIOR ART

Presently there is no known system for analyzing cotton for properties such as color, trash or moisture content as it flows through a gin in an air-entrained state.

SUMMARY

We now have developed a system for analyzing cotton as it flows through a gin. Generally the invention comprises moving flowable solids (or particulates), such as lint or seed cotton, through a duct, pipe, or similar conduit, abruptly halting part of the flowing solids, displacing or moving the halted solids in an arcuate pathway toward an interior surface of the conduit, and pressing the halted solids against the interior surface; wherein, during the halting step, much of the solids are permitted to pass through the conduit without being halted.

In the case of lint or seed cotton, the degree of pressing or compression is such that the mass of halted or captured cotton presents a face of uniform cotton density on that part of the mass which is pressed against said interior surface, wherein said uniform density is sufficient to enable the mass to be accurately analyzed by electromagnetic energy means such as optical or infrared scanners for at least one of the following properties: color, trash content, moisture content.

Ordinarily, the system is carried out in an intermittent or cyclic manner, so that a different mass of cotton, but a mass of essentially the same density each time, is pressed against said interior surface at time intervals; and, after compression, the pressure is removed, and each mass is allowed to resume its pathway through the conduit.

As used in the specification and claims, the phrase, "a face of uniform cotton density," in reference to the mass of cotton being pressed against said interior surface, means that the face of the mass which is pressed against the surface essentially is filled with cotton and impurities, with no voids. In other words, the mass is sufficiently compressed so that its flattened face essentially is completely occupied by cotton and impurities. This enables an optical or other analyzer adjacent the flattened face to make an analysis thereof, through, for example, a lens or window, which measurement is an accurate reflection of such properties of the mass as color, trash content, and moisture content.

In the case of a cotton gin, the cotton may be rapidly passing through the conduit, in an upward, downward, or lateral direction, at speeds of about 1000–5000 or more feet per minute, or at free-fall speeds. The device may be incorporated into any duct or pipe in a gin, or in a textile mill.

The present invention allows the cotton to be halted and compressed, while moving through a conduit, so as to present a face of uniform cotton density to an analyzing device.

An object of the present invention is to provide a system for halting, pressing, analyzing, and releasing flowable particulates or solids in a processing system, such as a ginning system.

Another object is to provide uniform cotton density on a face of the cotton mass to enable immediate and increased accuracy of analysis to be performed thereon, including color (e.g., yellowness and grayness), trash content (e.g., area and number of trash particles), leaf grade, and moisture content.

Another object is to intermittently or cyclically press different fractions or segments of flowable solids against an analyzer.

A further object is to intermittently or cyclically compress different cotton masses against an analyzer thereby enabling analysis to be carried out without removing samples from the system.

Yet another object is to provide analysis data that may be employed to automatically or manually adjust machine variables, so as to improve the final product.

A still further object is to provide portable and easily adaptable analysis equipment for any gin configuration.

Still another object is to provide uniform samples for grading.

An even further object is to provide color grade, trash grade, and moisture content of cotton continuously as it is processed at a gin.

Yet another object is to provide a mass of cotton of essentially the same density each time a mass is compresesed so as to provide a constant density of cotton for analysis at an adjacent or remote location.

Still further, an object is to provide an apparatus for analyzing flowable solids other than clumps of cotton, such as flowable particulate material, including seeds, man-made fibers, pharmaceuticals, coal, and so forth, that are flowing through a zone, but are not necessarily compressible; wherein small samples of the flowing material intermittently are pressed against an analyzer in the zone to be analyzed for properties such as size, impurities, shape, color, moisture. Depending upon the size of the particulates, the material does not necessarily essentially fill up the analysis window, with no voids, in the manner of compressible bulk cotton.

Yet further, an object is to provide a means of analyzing cotton as it is travelling through a conduit at high speeds in a gin, without removing it from the conduit.

Other objects and advantages will be obvious from the following more detailed description of the invention in which FIG. 1 illustrates a side sectional view of the basic elements of the invention.

DETAILED DESCRIPTION

Details of the invention will be described with regard to processing cotton, although the system may be employed for other flowable solids.

Figure 1:
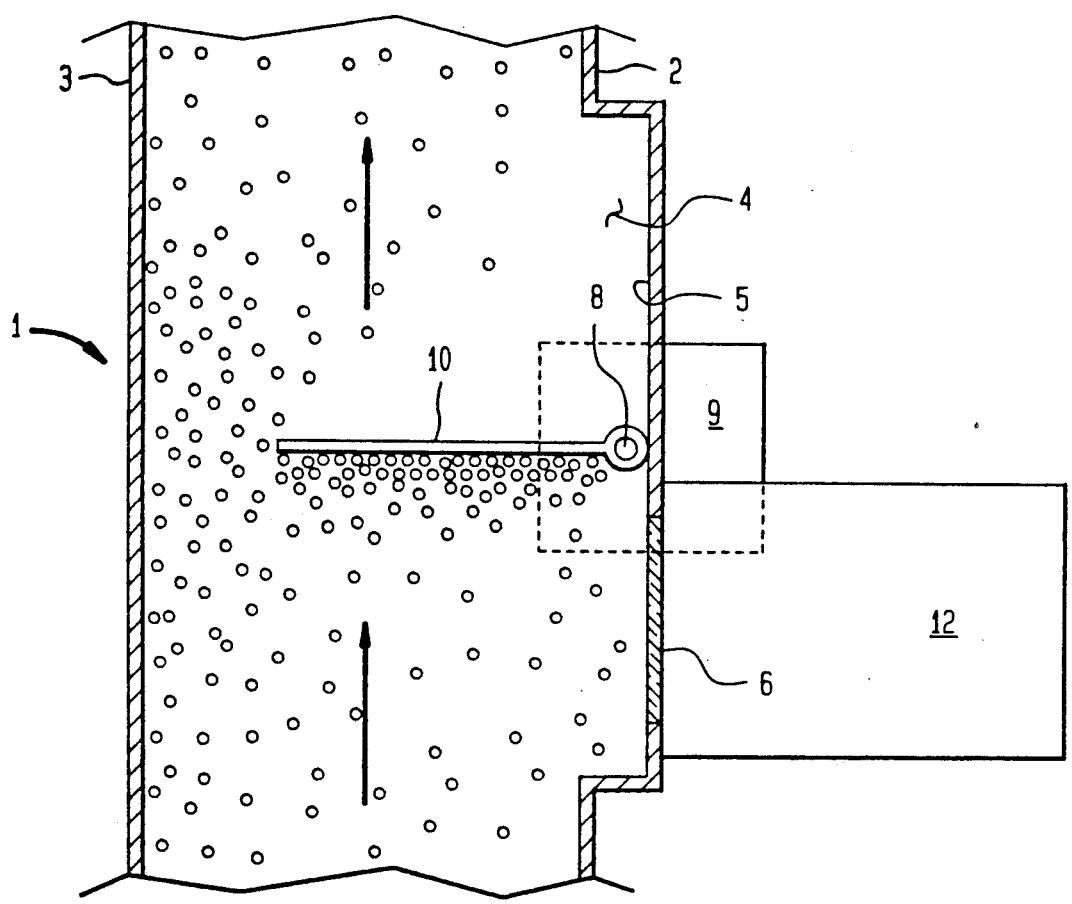
FIGS. 1a and 1b show different modes of operation of the baffle or plate of FIG. 1.

In FIG. 1, reference numeral 1 designates a typical rectangular duct in a ginning system, wherein the cotton is travelling upwardly toward, for example, a lint cleaner. The cotton ususally is moving rapidly at speeds of about 1000–5000 feet per minute, typically about 1500 feet per minute for lint cotton, and about 4500 feet per minute for seed cotton.

Reference numerals 2 and 3 designate the front and back walls of duct 1. The distance therebetween, or duct depth, typically is about 4–8 inches in the case of a lint duct; while full scale width typically is about 48-96 inches. For seed cotton, round ducts, having a diameter of about 12-24 inches, normally are used.

Figure 1B:
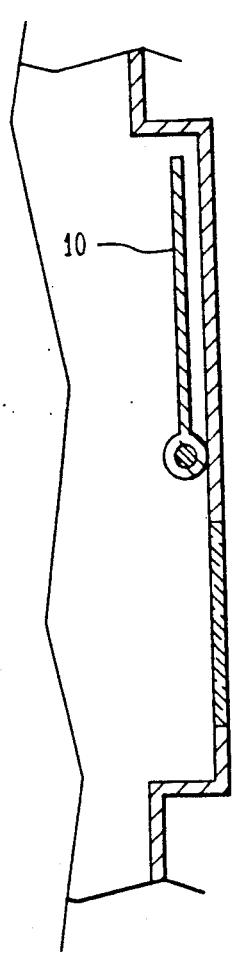
Figure 1A:
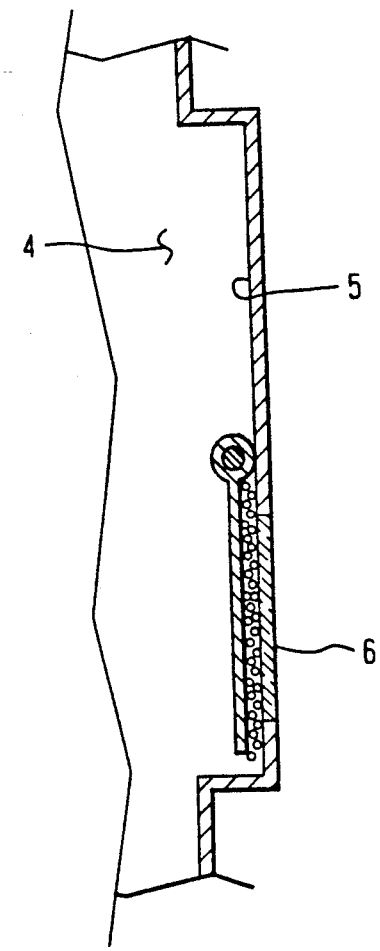

Provided in wall 2 is a recess 4. At the back of the recess is a surface 5 having a window or lens 6 therein. Positioned within the recess is a rotatable shaft 8 driven by a rotary actuator assembly 9. Rigidly attached to, or integral with shaft 8 is a plate or baffle 10, that is positioned in its solids-capturing or -halting mode in FIG. 1, i.e., the baffle projects transversely into the duct. FIGS. 1a and 1b illustrate the pressing and retracted-position modes, respectively, of plate 10. In these latter positions, plate 10 is positioned totally within recess 4 so as not to cause flow obstruction to cotton passing through the duct during compression or retraction.

Behind the window or lens 6 is an analyzing means schematically illustrated by reference numeral 12. One or more conventional analyzing instruments may be employed therein. Typically, the analyzing means employs electromagnetic energy (e.g., light, infrared) to detect properties of the seed cotton, such as color, trash content, and moisture content. Window or lens 6 is transparent to the extent to permit entry and reflection of electromagnetic rays of the analyzing device. In lieu of a window, the analyzing instrument itself, i.e., the lens portion thereof, may be inserted into an opening in the surface 5 of recess 4.

If two different analyzers are employed in a side-by-side manner, then two side-by-side windows or openings, or combinations of windows and openings, may be provided in surface 5, as opposed to one large window or opening. The size of the cotton mass being compressed or compacted thereagainst should be large enough to cover the single large window or opening, or both of the side-by-side windows or openings.

Conventional analyzers known in the cotton analysis art may be employed in the practice of the present invention, and include video cameras for trash content analysis and/or color analysis, as exemplified by the "Color/Trash Meter" made by Motion Control, Inc., and a similar device by Spinlab, Inc.; and infrared moisture sensors by Infrared Engineering, Inc., or Moisture Systems Corporation; and resistance devices for moisture analysis by Delmhorst, and similar devices by Cliff Granberry, Lummus Industries, or Continental Eagle Corporation.

Electrical signals from the camera analyzer are transmitted to a multiple serial port device (not shown) and then to a microcomputer (not shown). Analog signals from the moisture meter are transmitted to an analog-to-digital converter (not shown) and then to a computer. Data files to document the quality parameters are created by recording each data signal. An additional data file is created to produce a histogram for the data collected for each bale, module, or other increment.

Figure 2:
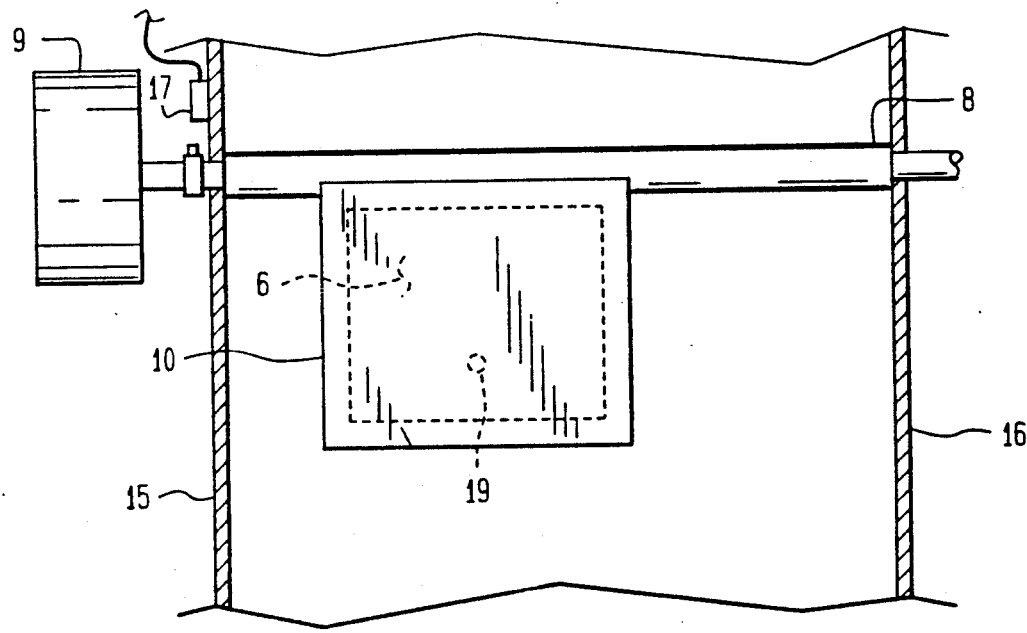
FIG. 2 is a front view of the plate of FIG. 1.

FIG. 2 illustrates a front view of plate 10 in its pressing mode, and also shows some details of rotary actuator assembly 9. The side walls of the duct are shown in this figure as reference numerals 15 and 16. As can be seen from both FIGS. 1 and 2, substantial quantities of the flowable solids, such as cotton, bypass plate 10 during the capturing and pressing steps, and pass through the duct without being halted. Only a small percentage of the cotton usually will be halted, displaced, and pressed against window 6, in comparison to the total volume of cotton travelling through duct 1. In many instances, over 90% of the cotton will pass through the duct without analysis.

Typical dimensions of plate 10, as viewed in FIG. 2, are about 6 inches high, and about 10 inches wide regardless of duct width. For such plate dimensions, shaft 8 typically will be at least 1 inch in diameter, and will extend the entire width of the duct. For a duct width of 60 inches, a shaft having a diameter of 1½ inches is suitable. To assure that compressed cotton totally covers the window 6, the window should be slightly smaller than the plate so that the plate overlaps each window boundary by about 1 inch. The plate, which may be solid or perforated, may be constructed of metal such as stainless steel or aluminum.

Generally speaking, hydraulics, pneumatics, or electric motors may be employed to activate rotary actuator assembly 9, pneumatics being preferred. In most instances, pneumatic pressures of about 75 to 150 psi are suitable for sufficiently compressing the cotton so as to provide a cotton face of uniform density at window 6. Under such pressure, the face of the cotton mass typically will experience a pressure of about 10 psi; and the mass ordinarily will be compressed to a thickness of about 1 inch.

Conventional heavy duty rotary actuator air cylinders capable of operating at 250 psi maximum are suitable for achieving such compression. Appropriate pneumatic hardware, including air control valves, solenoids, air supply, and related equipment will be obvious to those skilled in the art.

As to the details of rotary actuator assembly 9, it may include conventional catalogue hardware. Typically, the actuator transfers the linear motion of a hydraulic cylinder into a high torque rotary motion. Air pressure applied to a set of cylinders internally connected to a gear rack causes the rack to move back and forth. The rack engages a pinion gear which in turn rotates the pinion output shaft assembly in a predetermined rotational increment, in the present case being 180°. Integral flow controls provide rotational speed adjustment. Employing a 1½-inch bore shaft, inlet air pressures of about 60-80 psi provide torque outputs of 84-112 pounds, respectively. Dayton "Speedaire" model 2A121 is an exemplary pneumatic rotary actuator.

During operation, each cotton mass being analyzed at window 6 is forced to pause a very brief time, typically less than 0.5 second, to be analyzed at the window before resuming its passage through duct 1.

Off-the-shelf electronic time delay relays may be used to trigger the analyzing instruments to take readings only when compression of the cotton is at its maximum. For example, a relay with a timing range of 0.1 to 1.0 seconds may direct the capturing and compression cycle to start. The timer electrically may signal a directional solenoid air valve which further signals the pneumatic rotary actuator to activate.

A proximity switch 17 mounted on the duct, that is activated by a cam 18 on shaft 8 (see FIG. 2), sends an electrical signal to the analyzer's computer at the same time that the plate or baffle 10 reaches its maximum movement, thereby to define the precise time for the computer to take a reading. The time delay relay also allows a variable momentary pause after the proximity switch 17 is activated, typically 1 second, to ensure that the computer system receives a stable reading before the assembly begins its return.

Sufficient time is allowed for the assembly to fully rotate before the timer directs the rotary actuator to return. This time, typically 6 seconds, is used to delay the analyzer's computer from taking its reading until full rotation occurs. If full rotation of the shaft is not achieved before the preset time delay occurs such as when too large a sample of cotton is halted and prevents the rotary actuator from fully rotating, the assembly returns to its original position without analysis.

A preferred alternative means to trigger the analyzer's computer may be provided by a pressure or force transducer 19 on plate 10 or on surface 5 near window 6 that signals the computer to take a reading when adequate pressure to ensure uniform surface density is exerted on the sample.

In addition to analyzing for trash or moisture, the present invention may be employed to determine the diameter of cotton fibers, entanglement of fibers (neps), relative maturities of fibers, different kinds of impurities such as plant parts or soil particles, as well as dimensions of impurities.

Other types of analyzers, which do not require a window or lens in the wall surface, may be employed in the present invention. For example, that part of the wall surface on which the cotton mass is compressed may include electrode sensors that detect moisture.

In view of the fact that the plate-shaft-rotary actuator assembly of the present invention provides a mass of cotton having essentially the same density each time a mass is compressed against surface 5, some forms of analysis may be performed elsewhere than at the point of compression, whereby the mass, while being maintained under pressure, may be extracted from the initial point of compression by, for example, robotics, to be analyzed elsewhere. In this latter embodiment, the assembly functions to form a sample for remote analysis.

With further regard to this latter embodiment, if the amount of cotton passing through the duct is maintained at a substantially constant value, then the mass of cotton pressed against surface 5 on each cycle will be substantially the same quantity each time. Since some forms of cotton analysis require only a constant amount of material, rather than a face of uniform density, then in these instances, it will be unnecessary to maintain the sample under pressure during removal and transfer to the remote analyzer.

In the case of analyzing other flowable solids such as flowable particulates (as opposed to pieces of bulk cotton), the material may be permitted to flow downwardly through the zone by gravity; or it may flow horizontally or vertically through the zone by means of fluid entrainment or pressure differential.

I claim:

1. Apparatus for analyzing flowable solids comprising
   a. means to move said solids through a conduit;
   b. means connected to said conduit to abruptly halt part of said solids moving through said conduit, and thereafter to press said halted solids against an interior surface of said conduit;
   c. analyzing means adjacent said interior surface whereat said solids are pressed, to analyze said pressed solids; and
   d. means to remove pressure from said pressed solids after analysis thereof, and to permit said latter solids to resume movement through said conduit.

2. The apparatus of claim 1 including means to displace said halted solids in an arcuate pathway towards said interior surface prior to pressing.

3. The apparatus of claim 2 wherein said means to halt said solids includes means to intermittently halt solids moving through said conduit, while, during halting, permitting other solids to move through said conduit without being halted.

4. The apparatus of claim 3 wherein said halting, displacing, and compressing means comprises a moveable baffle within said conduit, and means to rotate said baffle.

5. The apparatus of claim 4 wherein said rotation means comprises a shaft connected along an edge of said baffle, and means to rotate said shaft about its axis.

6. The apparatus of claim 5 wherein part of said interior surface of said conduit is recessed with respect to the overall interior configuration of said conduit; wherein said shaft is positioned within said recess; and wherein said baffle is positionable totally within said recess.

7. Apparatus for analyzing cotton comprising
   a. means to move bulk cotton through a conduit;
   b. means connected to said conduit to halt a mass of said cotton moving through said conduit, and thereafter to press said halted mass against an interior surface in said conduit so that said halted mass may be analyzed; wherein, during halting, another mass of said cotton is permitted to pass through said conduit without being halted.

8. The apparatus of claim 7 further including cotton analyzing means adjacent said interior surface to analyze said pressed mass for a property selected from the group consisting of color, trash content, moisture content, and combinations thereof.

9. The apparatus of claim 7 wherein said means to halt said cotton includes means to intermittently halt cotton moving through said conduit.

10. The apparatus of claim 9 wherein said pressing means is sufficient to press said mass against said interior surface to form a face of uniform cotton density on that part of said mass which is pressed against said interior surface.

11. The apparatus of claim 10 further including cotton analyzing means adjacent said interior surface to analyze said face of said mass for a property selected from the group consisting of color, trash content, moisture content, and combinations thereof.

12. The apparatus of claim 10 including means to displace each halted mass in an arcuate pathway towards said interior surface prior to pressing.

13. The apparatus of claim 12 wherein said halting, displacing, and compressing means comprises a moveable baffle within said conduit, and means to rotate said baffle.

14. The apparatus of claim 13 wherein said rotation means comprises a shaft connected along an edge of said baffle, and means to rotate said shaft about its axis.

15. The apparatus of claim 14 wherein part of said interior surface of said conduit is recessed with respect to the overall interior configuration of said conduit; wherein said shaft is positioned within said recess; and wherein said baffle is positionable totally within said recess.

16. The apparatus of claim 15 further including cotton analyzing means adjacent said interior surface to analyze said face of said mass for a property selected from the group consisting of color, trash content, moisture content, and combinations thereof.

17. The apparatus of claim 16 wherein said analyzing means comprises
   a. lens means in said interior surface whereat said mass is pressed, so that said mass is pressed against said lens means; and b. optical analyzing means adjacent said lens means to determine color and trash level in said mass of cotton pressing against said lens means.

18. The apparatus of claim 16 wherein said analyzing means comprises electrode means adjacent said interior surface whereat said mass is pressed, so that said mass is pressed against said electrode means.

19. The apparatus of claim 17 further including infrared analyzing means adjacent said lens means.

20. A process for analyzing bulk cotton that is moving through a conduit comprising halting a mass of said cotton moving through said conduit, and thereafter pressing said halted mass against an interior surface in said conduit with sufficient force so that said mass presents a face of uniform cotton density on that part of said mass which is pressed against said interior surface, so that said mass may be analyzed accurately for at least one of the following properties: color, trash content, moisture content.

21. The process of claim 20 further including analyzing said face for a property selected from the group consisting of color, trash content, moisture content, and combinations thereof.

22. The process of claim 21 wherein said halting and pressing steps comprise intermittently halting and pressing cotton against said interior surface at time intervals.

23. The process of claim 22 further comprising displacing each halted mass in an arcuate pathway towards said interior surface prior to pressing.

24. The process of claim 23 wherein said analyzing step employs electromagnetic energy to analyze said mass.

25. The process of claim 23 wherein said halting, displacing, and pressing steps comprise moving a baffle transversely into the pathway of said bulk cotton so as to capture a mass of cotton on said baffle, and rotating said baffle so as to press said captured mass against said interior surface.

26. A process for analyzing cotton as it is travelling through a conduit in a gin without removing it from said conduit, comprising halting the flow of part of said cotton within said conduit, while permitting the remaining part to continue travelling therethrough, moving said halted part of said cotton in an arcuate pathway to an analyzing zone within said conduit; thereafter analyzing said halted part within said conduit for a property selected from the group consisting of color, trash content, moisture content, and combinations thereof; subsequently permitting said halted part to resume its travel through said conduit; and unobstructedly passing additional cotton through said conduit prior to said halting step and during said analyzing step.

27. The process of claim 26 wherein said cotton is travelling at a speed of at least 1000 feet per minute through said conduit.

28. A process for analyzing cotton as it is travelling through a conduit in a gin at a speed of at least 1000 feet per minute without removing it from said conduit, comprising halting the flow of part of said cotton within said conduit, as it is travelling at a speed of at least 1000 feet per minute, while permitting the remaining part to continue travelling therethrough, moving said halted part of said cotton to an analyzing zone within said conduit; thereafter analyzing said halted part within said conduit for a property selected from the group consisting of color, trash content, moisture content, and combinations thereof; subsequently permitting said halted part to resume its travel through said conduit; and unobstructedly passing additional cotton through said conduit prior to said halting step and during said analyzing step.

29. A process for analyzing cotton as it is travelling upwardly through a conduit in a gin without removing it from said conduit, comprising halting the flow of part of said cotton within said conduit, while permitting the remaining part to continue travelling upwardly therethrough, moving said halted part of said cotton in an arcuate pathway to an analyzing zone with said conduit; thereafter analyzing said halted part within said conduit for a property selected from the group consisting of color, trash content, moisture content, and combinations thereof; and subsequently permitting said halted part to resume its upward travel through said conduit.

30. A process for analyzing cotton as it is travelling upwardly through a conduit in a gin at a speed of at least 1000 feet per minute without removing it from said conduit, comprising halting the flow of part of said cotton within said conduit, as it is travelling at a speed of a least 1000 feet per minute, while permitting the remaining part to continue travelling upwardly therethrough, moving said halted part of said cotton to an analyzing zone within said conduit; thereafter analyzing said halted part within said conduit for a property selected from the group consisting of color, trash content, moisture content, and combinations thereof; and subsequently permitting said halted part to resume its upward travel through said conduit.

* * * * *